(12) United States Patent
Felix et al.

(10) Patent No.: US 12,154,701 B2
(45) Date of Patent: Nov. 26, 2024

(54) SEALED CONTAINER PROVIDED WITH A BI-MATERIAL FLANGE

(71) Applicant: ABC TRANSFER, Tours (FR)

(72) Inventors: Julien Felix, Tours (FR); Jean-Luc Schneider, Sligo (FR); Thierry Girard, Tours (FR)

(73) Assignee: ABC TRANSFER, Tours (FR)

( * ) Notice: Subject to any disclaimer, the term of this patent is extended or adjusted under 35 U.S.C. 154(b) by 336 days.

(21) Appl. No.: 17/787,477

(22) PCT Filed: Dec. 18, 2020

(86) PCT No.: PCT/FR2020/052562
§ 371 (c)(1),
(2) Date: Jun. 20, 2022

(87) PCT Pub. No.: WO2021/123687
PCT Pub. Date: Jun. 24, 2021

(65) Prior Publication Data
US 2023/0043324 A1 Feb. 9, 2023

(30) Foreign Application Priority Data

Dec. 20, 2019 (FR) ..................................... 1915264

(51) Int. Cl.
*G21F 7/005* (2006.01)
*B01J 3/03* (2006.01)
*B01L 1/02* (2006.01)
*B01L 3/00* (2006.01)
*C12M 1/12* (2006.01)
(Continued)

(52) U.S. Cl.
CPC ................ *G21F 7/005* (2013.01); *B01J 3/03* (2013.01); *B01L 1/02* (2013.01); *B01L 3/508* (2013.01);
(Continued)

(58) Field of Classification Search
CPC .... G21F 7/005; G21F 5/12; B01J 3/03; B01L 1/02; B01L 3/508; B01L 2200/025;
(Continued)

(56) References Cited

U.S. PATENT DOCUMENTS 4,669,628 A * 6/1987 Hatta ...................... E05F 15/42
49/54
5,853,207 A * 12/1998 Saint Martin ........... G21F 7/005
292/257
(Continued)

*Primary Examiner* — David A Vanore
(74) *Attorney, Agent, or Firm* — McDonnell Boehnen Hulbert & Berghoff LLP

(57) ABSTRACT

The invention relates to a sealed container (1) comprising a container body (2) having a through-hole (8) that is delimited by a flange and is closed by a removable door (7) mounted on the flange and an annular seal located between the flange and the door (7), characterized in that the flange consists of two separate concentric sleeves, one of the sleeves defining an outer flange body (5) arranged to allow a connection of the container body (2) to a flange having a complementary shape on an enclosure, the other sleeve defining an inner flange body (6) arranged to allow a connection of the door (7) to the flange, the outer flange body (5) being made entirely or partially of a resistant plastic material selected from plastics that are resistant to autoclave sterilization cycles, while the inner flange body (6) is made of a metal alloy.

8 Claims, 4 Drawing Sheets

(51) Int. Cl.
  *F16J 13/12* (2006.01)
  *F16J 15/06* (2006.01)
  *G21F 5/12* (2006.01)

(52) U.S. Cl.
  CPC .............. *C12M 37/04* (2013.01); *F16J 13/12* (2013.01); *F16J 15/061* (2013.01); *G21F 5/12* (2013.01); *B01L 2200/025* (2013.01); *B01L 2200/026* (2013.01); *B01L 2200/0689* (2013.01); *B01L 2300/046* (2013.01)

(58) Field of Classification Search
  CPC ....... B01L 2200/026; B01L 2200/0689; B01L 2300/046; C12M 37/04; F16J 13/12; F16J 15/061
  See application file for complete search history.

(56) References Cited

U.S. PATENT DOCUMENTS

| | | | |
|---|---|---|---|
| 2016/0201382 A1* | 7/2016 | Dufour | E05C 19/00 49/68 |
| 2016/0208527 A1* | 7/2016 | Dufour | G21F 7/005 |
| 2016/0281418 A1* | 9/2016 | Dufour | B01L 1/02 |
| 2021/0293337 A1* | 9/2021 | Belin | F16J 15/32 |
| 2022/0178172 A1* | 6/2022 | Felix | E05B 65/006 |
| 2022/0371001 A1* | 11/2022 | Felix | F16J 13/18 |
| 2022/0371011 A1* | 11/2022 | Felix | G21F 5/12 |
| 2022/0396403 A1* | 12/2022 | Felix | B65B 5/045 |
| 2022/0397195 A1* | 12/2022 | Felix | G21F 7/005 |
| 2023/0026497 A1* | 1/2023 | Felix | B65B 39/08 |
| 2023/0043324 A1* | 2/2023 | Felix | B01L 1/02 |

* cited by examiner

12,154,701 B2

SEALED CONTAINER PROVIDED WITH A BI-MATERIAL FLANGE

CROSS REFERENCE TO RELATED APPLICATION

This application is a U.S. National Phase of International Application No. PCT/FR2020/052562 filed Dec. 18, 2020, which claims priority to French Patent Application No. FR1915264, filed Dec. 20, 2019, both of which are incorporated by reference herein in their entirety.

TECHNICAL FIELD OF THE INVENTION

The invention relates to the field of containers intended to be connected in a sealed manner to sterile enclosures so as to allow their respective volumes to be placed in communication without contact with said external environment.

The invention relates more particularly to a sealed container comprising a container body having a through-hole delimited by a flange and closed by a removable door mounted on the flange, an annular seal being located between the flange and the door.

The sealed container according to the invention is intended in particular, but not exclusively, for the transfer of dangerous products such as certain pharmaceutical, biotechnological, biological, chemical or radioactive products, the transfer of components such as stoppers, bottles, pistons, syringes, etc., the transfer of environmental control devices such as culture medium racks, particle counters, etc., the transfer of cleaning systems, the transfer of liquids, powders, tools, the transfer of waste to the outside of the enclosure and/or the transfer of any element necessary for the production or maintenance of the production line.

PRIOR ART

In a known manner, the connection of a sealed container to a sterile enclosure for the transfer of products, without breaking the connection and the seal, is carried out using two connection devices, one equipping the container and the other equipping the enclosure. Each connection device comprises a flange respectively delimiting the through-hole in the internal volume of the container or of the enclosure, each of the through-holes being closed off by a door. The flange and the door of the container are capable of being connected respectively to the flange and to the door of the enclosure by a bayonet connection to one another under the action of a rotational movement of the associated flange and door of the container with respect to the flange and door of the enclosure to which they are attached. Thus, the flanges and the doors, respectively, of the container and of the enclosure are respectively provided with notches and with internal or external lugs.

During the rotational movement, the container door is disengaged from the associated flange.

Usually, the flanges of the containers and the enclosures are made of stainless steel. Such flanges, however, have the drawback of being subject to seizing effects. During their connection, the stainless steel flanges undergo significant friction caused by the roughness of their surface in contact, which can lead over time to the tearing of material at these surfaces and thus cause the seizing thereof.

In order to overcome this problem of stainless steel/stainless steel seizing when connecting the flanges together, rollers and pads are inserted in the lugs of each of the flanges. However, this type of container encounters several problems.

One of the problems encountered with this type of container is the blocking and wear of the rollers caused by friction, the autoclave and the washing of the containers. It is therefore necessary to carry out regular maintenance of these rollers.

Another problem encountered is the dismantling of the rollers. Over time, the axles of the rollers by which they are attached can seize up and therefore prevent their disassembly, their small relative size not allowing the use of an appropriate extraction tool.

Another problem encountered is improper handling of the containers, which can in some cases lead to irreversible damage thereto. In addition to the deformations of the container body, the deformations of the external lugs of the flanges can in particular lead to the container becoming unusable, the latter no longer being able to be connected to an enclosure.

In an attempt to overcome these problems, application WO2013/110745 has proposed a container whose flange is provided with removable lugs made of an antifriction material, such as a plastic material, for example. One of the drawbacks of such an arrangement is that it requires tedious and somewhat difficult maintenance (many parts to be disassembled).

The invention aims to remedy these problems by proposing a sealed container reducing the risks of seizing when it is connected to an enclosure while offering easier maintenance and thus a longer life than the containers of the prior art.

Another object of the invention is to provide a sealed container having a compact connection device, devoid of any water retention zone.

Another object of the invention is to propose a sealed container that is robust and durable in its use, but also resistant over time to sterilization by autoclave and repeated washing, as well as to offer improved cleanability.

SUBJECT MATTER OF THE INVENTION

To this end, the invention proposes a sealed container comprising a container body having a through-hole that is delimited by a flange and is closed by a removable door mounted on the flange, an annular seal located between the flange and the door, the flange, the door and the seal forming a sealed connection device connectable to a complementary connection device of a sterile enclosure so as to allow sterile communication between the sealed container and the sterile enclosure, the container being remarkable in that the flange consists of two separate coaxial sleeves, one of the sleeves defining a so-called outer flange body comprising connection means to allow connection of the container body to the complementary enclosure, the other sleeve defining a so-called inner flange body to allow the door to be connected to the flange, the outer flange body being made entirely or partially of a resistant plastic material selected from plastics that are resistant to autoclave sterilization cycles, while the inner flange body is made of a metal alloy.

Thus, a bi-material flange comprising a plastic part chosen from plastics that are resistant to sterilization cycles in the associated autoclave and a metal alloy part makes it possible to overcome the problem of seizing encountered with the containers of the state of the art. This also makes it possible to ensure sterilization of the container at autoclave temperatures (of the order of 135° C.) without increasing the treatment time. This also makes it possible to offer simple and rapid maintenance of the connection device. This also improves the cleanability of the container, as the openings needed for the rollers in the containers of the state of the art are no longer required. According to the invention, the flange consists of only two parts, the means for connecting the container body to the enclosure and the means for connecting the door to the flange being formed in one piece with one of these parts, respectively. Thus, the means for connecting the container body to the enclosure are formed integrally with the outer flange body, while the means for connecting the door to the flange being formed integrally with the inner flange body. The outer flange body is assembled on the inner flange body, advantageously in a removable manner (reversible assembly). This thus makes it possible to easily and reversibly dismantle the outer flange body, which corresponds to the part of the flange that is most exposed to handling errors. The outer flange body is thus interchangeable in the event of alteration. It thus becomes a spare part, so that the containers formed in this way with a bi-material flange, the outer part of which is made of plastic, have a longer life than that of containers with flanges made of stainless steel.

Advantageously, the outer flange body is assembled to the inner flange body by assembly screws mounted on the front face of the container.

Advantageously, the outer flange body and the inner flange body delimit a radial groove receiving a disc heel of the seal.

Advantageously, the inner flange body has an internal face arranged to form a liquid flow ramp toward the interior of the container body.

Advantageously, the outer flange body is made of PEEK (polyetheretherketone).

Advantageously, the inner flange body is formed in one piece with the container body.

Advantageously, the inner flange body is made of stainless steel.

BRIEF DESCRIPTION OF THE DRAWINGS

Other features and advantages of the invention will become apparent from the following detailed description of the invention with reference to the appended figures, in which.

DETAILED DESCRIPTION OF THE INVENTION

Figure 1:
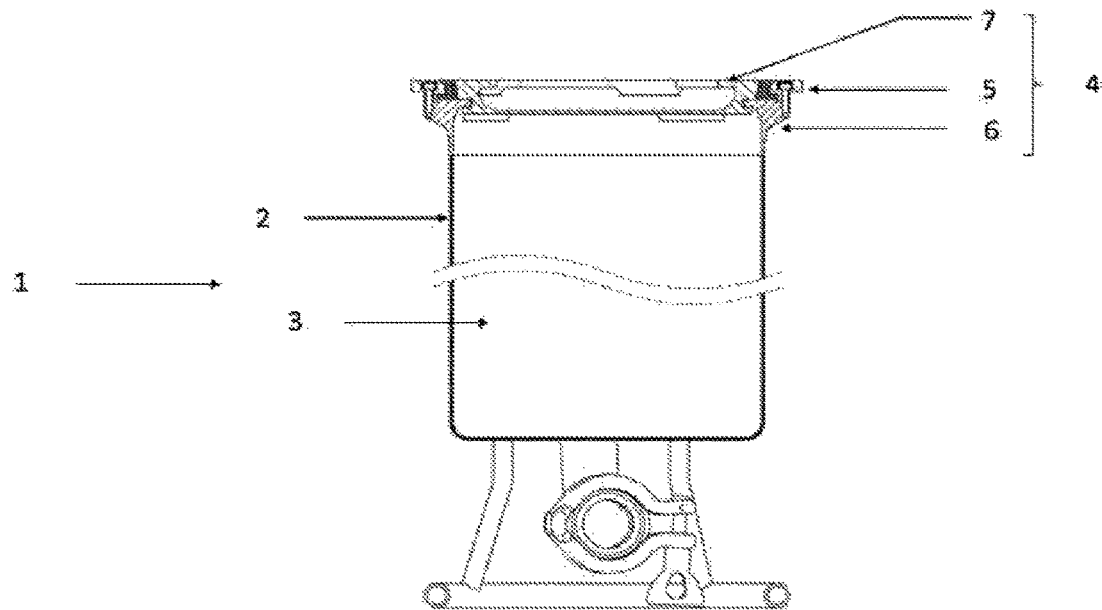
FIG. 1 shows a schematic sectional view of a container according to the invention.
Figure 2:
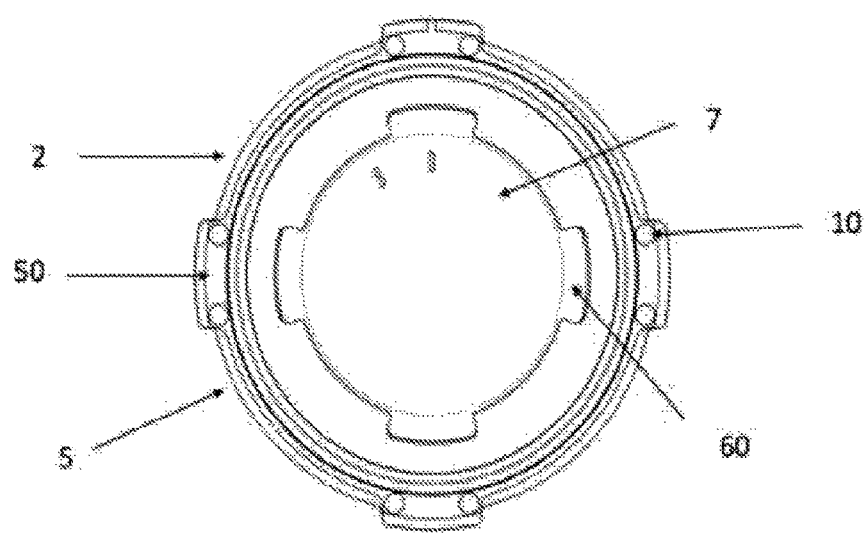
FIG. 2 shows a top view of the container of FIG. 1.

In the following, the terms "exterior," "external," "interior" and "internal" are defined with respect to the container. Thus, the terms "exterior" and "external" designate what is located outside the interior space of the container, the farthest from the interior space or directed away from the interior of the enclosure, and "interior" and "internal" designate that which is located in the interior space, closest to the interior space or directed toward the interior of the container.

In relation to FIGS. 1 to 6, a container 1 is described comprising a rigid container body 2, advantageously made of stainless steel, arranged to define an internal volume 3 and a through-hole 8.

The container 1 also comprises a sealed connection device 4 that is capable of cooperating with a complementary connection device fitted to an enclosure. The connection devices are arranged so as to ensure sterile communication between the internal volume 3 of said container 1 and that of the enclosure when the container is connected to the enclosure.

The connection device 4 comprises a flange delimiting the through-hole 8 and a removable door 7 attached to the flange so as to close the through-hole 8. According to the invention, the flange consists of two sleeves 5, 6 that are separate and independent of each other. These sleeves 5, 6 are coaxial, the sleeve 6 advantageously being engaged in the sleeve 5. The sleeve 5 defines a so-called outer flange body 5 that is arranged to allow connection of the container body 2 to the enclosure. The other sleeve 6 in turn defines a so-called inner flange body 6 arranged to allow connection of the door 7 to the flange. The term "outer flange body" designates the flange body furthest from the interior space of the container. By analogy, the term "inner flange body" designates the flange body closest to the interior space of the container. In the example shown, the sleeve 6 is partially engaged in the sleeve 5. This is an example of an arrangement, it being understood that an arrangement may be provided in which the sleeves 5, 6 are arranged concentrically with respect to each other.

The connection device 4 comprises connection means, of the bayonet type, for connecting the container 1 to an enclosure. Thus, the flange 5, 6 and the door 7 of the container respectively comprise an arrangement of external and internal lugs 50 and 70, and notches 51 and 71, complementary to an arrangement of lugs and notches equipping the enclosure and forming a complementary connection device.

In the example illustrated, the door 7 is assembled to the flange also by bayonet-type connection means. Thus, the door 7 comprises an arrangement of external lugs 72 and notches 73 cooperating with an arrangement of internal lugs 60 and notches 61 borne by the flange.

As illustrated in the figures, the outer flange body 5 bears the outer lugs 50 of the bayonet system while the inner flange body 6 bears the radial inner lugs 60 allowing the door 7 to be retained on the flange. The outer lugs 50 and the inner lugs 60 are formed integrally with the flange bodies bearing them, respectively.

In order to limit friction, the outer flange body 5 is made entirely or partially from a plastic material. The plastic material will be chosen from plastics to withstand autoclave sterilization cycles. Advantageously, the outer flange body 5 will be made of PEEK.

The inner flange body 6 is made of the same material as the container body 2. Advantageously, it is made of stainless steel. In the example shown, the inner flange body 6 is formed integrally with the container body 2.

The outer flange body 5 is assembled on the inner flange body 6 in a removable manner. In the illustrated embodiment, the outer flange body 5 is assembled to the inner flange body 6 by attachment means such as assembly screw 10 as shown in the example, which pass through the outer lugs 50 of the outer flange body 5. The outer flange body 5 and the inner flange body 6 are assembled by the front face of the container. "Front face" means the face of the container that is intended to be placed facing the enclosure. Advantageously, the assembly screws 10 are hidden by covers 11 that are flush with the front face of the outer flange body 5. The covers 11 are preferably made of plastic material in order to facilitate friction, and preferably of the same material as that of the outer flange body. In the example described, the covers are made of PEEK.

The container 1 further comprises an annular seal 13 borne by the flange. The seal 13 is coupled directly to the flange 5, 6. Said seal 13 has an annular seal body, advantageously of parallelepipedal section, extended on its outer periphery by a disc heel 14 enclosed in a groove delimited by the outer flange body 5 and the inner flange body 6. The annular seal body advantageously has a front sealing face 13A in contact with the rear face of the outer seal body 16 and a lateral sealing face 13B intended to be in contact with the door 7 when the latter is in its position closing the through-hole 8. Thus, when the door 7 is in the closed position, the annular seal 13 is located in the space delimited by the outer flange body 5, the inner flange body 6 and the door 7. Advantageously, the sealing faces 13A and 13B are not smooth so as to promote friction when connecting the container to the enclosure, thus improving the connection forces. This also makes it possible to limit the friction between the surface of the seal and the contact surface of the flange or of the door, as the appropriate. The sealing faces can thus be provided with scores, ribbed forms, teeth, pins or can have a surface condition that promotes friction. The seal 13 is made of a silicone material or other materials that minimize the effect of remanence. Provision may also be made for the seal to be made of a bacteriostatic material.

The shape of the seal 13 and its arrangement with the door and the flange allow creation of a "full" sealing zone, that is to say, without a cavity or void (referred to as "hidden zones"), unlike the prior art seals, which have such zones that promote the retention of washing liquids and bacteria.

Figure 3:
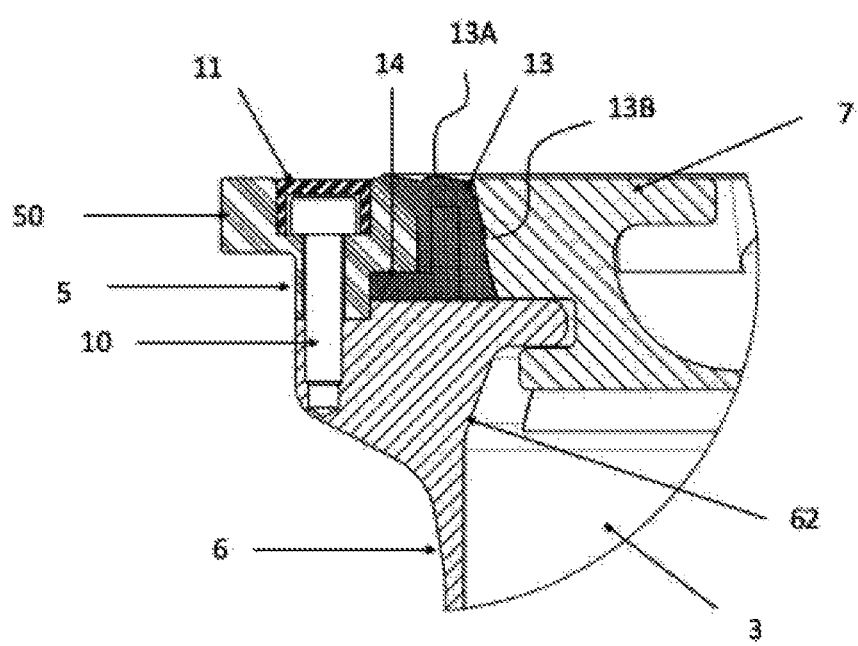
FIG. 3 shows a detail view of the container of FIG. 1.
Figure 5:
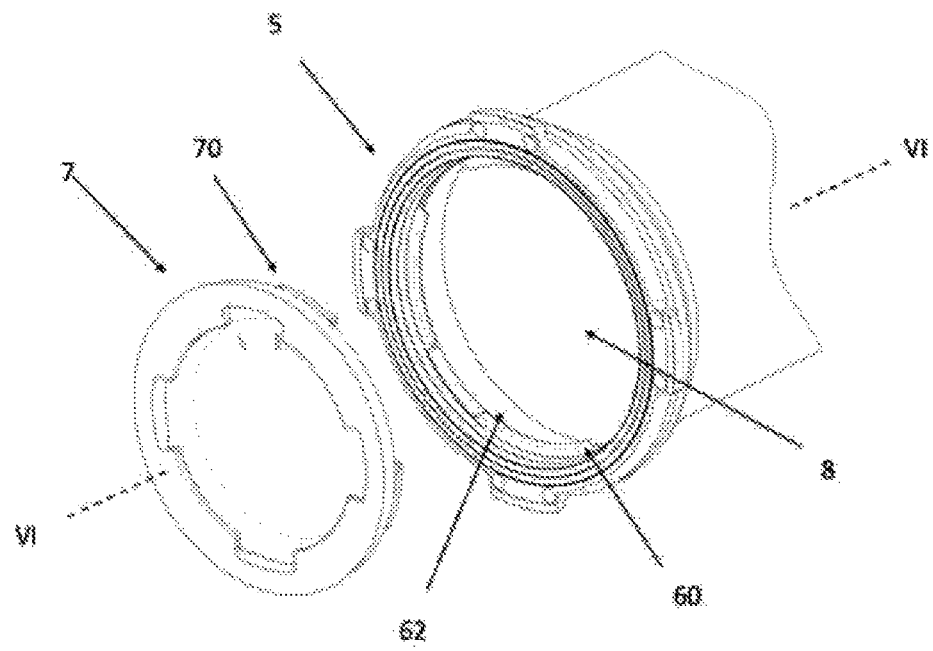
FIG. 5 shows a side perspective front view of the container of FIG. 1, with the door shown removed from the container.
Figure 6:
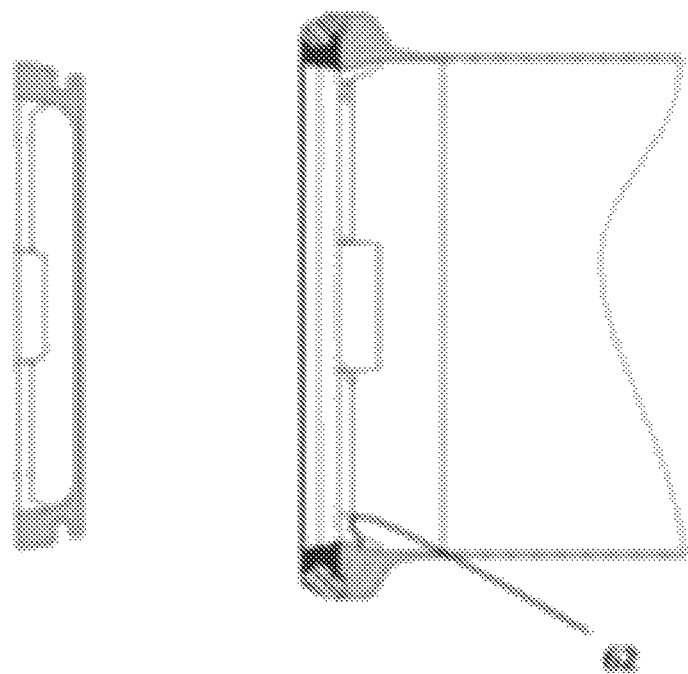
FIG. 6 shows a sectional view along axis VI-VI of the container of FIG. 5.

In order to improve the flow of the washing liquid, the inner flange body 6 advantageously has an internal face 62 arranged to form a ramp for the flow of liquid toward the interior of the container body 1 as illustrated in FIGS. 3, 5 and 6.

In the above, the container body 2 is rigid. It is of course obvious that the container 1 according to the invention is not limited to this type of container 1 and that a container body 2 may be provided, for example, in the form of a flexible pouch. In this case, the flexible pouch will advantageously be held engaged between the outer flange body 5 and the inner flange body 6.

Figure 4:
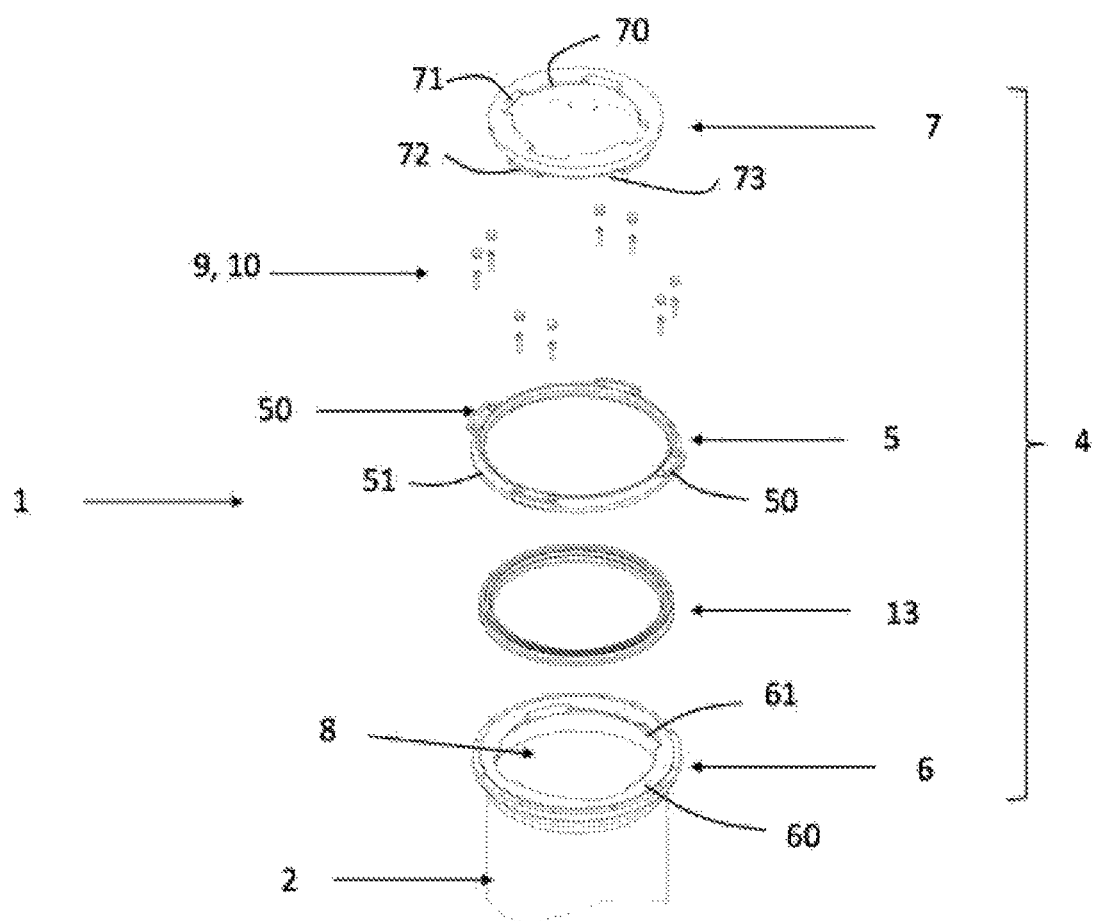
FIG. 4 shows an exploded view of the container of FIG. 1.

Due to the arrangement of its component elements, the connection device is assembled by simple clipping of the elements according to the stack illustrated in FIG. 4.

The invention is described in the foregoing by way of example. It is understood that a person skilled in the art is in a position to produce various variant embodiments of the invention without thereby departing from the scope of the invention.

The invention claimed is:

1. A sealed container comprising:
a container body having a through-hole delimited by a flange and closed by a removable door mounted on the flange, and
an annular seal located between the flange and the door, the flange, the door and the seal forming a sealed connection device connectable to a complementary connection device of a sterile enclosure so as to allow sterile communication between the sealed container and the sterile enclosure,
characterized in that the flange consists of two separate coaxial sleeves,
one of the sleeves, defining an outer flange body, comprising connection means to allow connection of the container body to the sterile enclosure, and
the other sleeve, defining an inner flange body, comprising connection means to allow connection of the door to the flange,
the outer flange body being made entirely or partially of a resistant plastic material chosen from plastics resistant to autoclave sterilization cycles, while the inner flange body is made of a metal alloy.

2. The sealed container according to claim 1, characterized in that the outer flange body is assembled on the inner flange body in a removable manner.

3. The sealed container according to claim 1 of claim 2, characterized in that the outer flange body is assembled to the inner flange body by assembly screws mounted on the front face of the container.

4. The sealed container according to claim 1, characterized in that the outer flange body and the inner flange body delimit a radial groove receiving a disc heel of the seal.

5. The sealed container according to claim 1, characterized in that the inner flange body has an internal face arranged to form a liquid flow ramp toward the interior of the container body.

6. The sealed container according to claim 1, characterized in that the outer flange body is made of PEEK (polyetheretherketone).

7. The sealed container according to claim 1, characterized in that the inner flange body is formed in one piece with the container body.

8. The sealed container according to claim 1, characterized in that the inner flange body is made of stainless steel.

* * * * *